US012201593B2

(12) United States Patent
Lee et al.

(10) Patent No.: US 12,201,593 B2

(45) Date of Patent: Jan. 21, 2025

(54) ORAL PHARMACEUTICAL FORMULATIONS OF BITTER COMPOUNDS FOR ASTHMA

(71) Applicant: Aardvark Therapeutics Inc., San Diego, CA (US)

(72) Inventors: Tien-Li Lee, San Diego, CA (US); Zhenhuan Zheng, San Diego, CA (US)

(73) Assignee: Aardvark Therapeutics Inc., San Diego, CA (US)

( * ) Notice: Subject to any disclaimer, the term of this patent is extended or adjusted under 35 U.S.C. 154(b) by 934 days.

(21) Appl. No.: 17/256,212

(22) PCT Filed: Jul. 2, 2019

(86) PCT No.: PCT/US2019/040432

§ 371 (c)(1),
(2) Date: Dec. 27, 2020

(87) PCT Pub. No.: WO2020/010166

PCT Pub. Date: Jan. 9, 2020

(65) Prior Publication Data

US 2021/0161838 A1 Jun. 3, 2021

Related U.S. Application Data

(60) Provisional application No. 62/693,255, filed on Jul. 2, 2018.

(51) Int. Cl.

| | |
|---|---|
| ***A61K 31/167*** | (2006.01) |
| ***A61K 9/00*** | (2006.01) |
| ***A61K 31/136*** | (2006.01) |
| ***A61P 11/06*** | (2006.01) |

(52) U.S. Cl.

CPC .......... *A61K 31/167* (2013.01); *A61K 9/0053* (2013.01); *A61K 31/136* (2013.01); *A61P 11/06* (2018.01)

(58) Field of Classification Search

CPC .................................................... A61K 31/167

See application file for complete search history.

(56) References Cited

U.S. PATENT DOCUMENTS 6,068,833 A * 5/2000 Aberg .................... A61K 31/47 514/937
7,939,671 B2 5/2011 Li
8,062,627 B2 * 11/2011 Aberg .................. A61K 31/167 424/443
8,445,692 B2 5/2013 Karanewsky
8,796,233 B2 8/2014 Goddard
9,272,051 B2 3/2016 Goddard
9,579,315 B2 * 2/2017 Liggett ................ A61K 31/167
10,330,678 B2 6/2019 Goddard
10,610,500 B2 4/2020 Pharma
10,835,505 B2 11/2020 Lee
2013/0131108 A1 5/2013 Ligget et al.
2014/0030332 A1 1/2014 Baron
2014/0302528 A1 10/2014 Li
2017/0227548 A1 8/2017 Henkin
2018/0161298 A1 6/2018 Deretic

FOREIGN PATENT DOCUMENTS

WO WO2008/024490 2/2008
WO WO2012021291 A2 * 2/2012
WO WO2016/172479 10/2016

OTHER PUBLICATIONS

Berge et al. J Pharm Sci. Jan. 1977;66(1):1-19, published Jan. 1, 1977 (Year: 1977).*

Souter et al., United States Patent Application Publication US 2015/0252304 A1, Pub. Date: Sep. 10, 2015, pp. 1-13 (Year: 2015).*

Kumar et al. (Pharmaceutical Technology, Mar. 2008, 32, 3). (Year: 2008).*

Zhai et al. "Activation of bitter taste receptors (tas2rs) relaxes detrusor smooth muscle and suppresses overactive bladder symptoms" Oncotarget :21156-21167, 2016.

Deckmann et al., "Bitter triggers acetylcholine release from polymodal urethral chemosensory cells and bladder reflexes " Proc. Natl. Acad. Sci. 111:8287-8292, 2014.

Upadhyaya et al., PLOS One 9:e110373, Dextromethorphan Mediated Bitter Taste Receptor Activation in the Pulmonary Circuit Causes Vasoconstriction.

Manson et al., "Bitter taste receptor agonists mediate relaxation of human and rodent vascular smooth muscle " Eur. J. Pharmacology 740:302-311, 2014.

Pulkkinen et al., "The bitter taste receptor (TAS2R) agonists denatonium and chloroquine display distinct patterns of relaxation of the guinea pig trachea" Am. J. Physiol. Lung Cell Mol. Physiol. 303:956-966, 2012.

Sai et al. "Bitter tastants induce relaxation of rat thoracic aorta precontracted with high K+" Clin. Exper. Pharmacology and Phys. 41:301-301, 2014.

Gassin-Delyle et al., "The expression and relaxant effect of bitter taste receptors on human bronchi" Respiratory Research 14:134, 2013.

Deloose et al. "Intragastric infusion of denatonium benzoate attenuates interdigestive gastric motility and hunger scores in healthy female volunteers1" Am. J. Clin. Nutr. 105:583-588, 2017.

Avau et al. "Targeting extra-oral bitter taste receptors modulates gastrointestinal motility with effects on satiation" Scientific Reports 5:15985 2015.

(Continued)

*Primary Examiner* — Umamaheswari Ramachandran
(74) *Attorney, Agent, or Firm* — McNeill PLLC

(57) ABSTRACT

There is disclosed an oral pharmaceutical formulation of bitter compounds that are agonists of TAS2R receptors for the treatment of asthma. More specifically, the present disclosure provides an asthma oral formulation comprising a bitter agent selected from the group consisting of denatonium benzoate (DB), denatonium chloride (DC), denatonium saccharide (DS), denatonium acetate (DA), and combinations thereof and formoterol.

12 Claims, 4 Drawing Sheets

(56) References Cited

OTHER PUBLICATIONS

Avau et al.2 "The Gustatory Signaling Pathway and Bitter Taste Receptors Affect the Development of Obesity and Adipocyte Metabolismi n Mice" PLOS One 10.1371 2015.
Glendinning et al., "Intragastric infusion of denatonium conditions flavor aversions and delays gastric emptying in rodents" Physiol. Behav. 93:757-765, 2008.
Hao et al., "Role of CCK1 and Y2 receptors in activation of hindbrain neurons induced by intragastric administration of bitter taste receptor ligands" Am. J. Physiol. Regul. Integr. Comp. Physiol. 294:R33-R38, 2008.
Janssen et al., "Bitter taste receptors and a-gustducin regulate the secretion of ghrelin with functional effects on food intake and gastric emptying " PNAS 108:2094-2099, 2011.
Kim et al., "Denatonium induces secretion of glucagon-like peptide-1 through activation of bitter taste receptor pathways" Diabetologia 57:2117-2125, 2014.
Miyata et al. "Effect of five taste ligands on the release of CCK from an enteroendocrine cell line, STC-1" Biomedical Research 35:171-176, 2014.
Schier et al. "Ongoing ingestive behavior is rapidly suppressed by a preabsorptive, intestinal "bitter taste" cue" Am. J. Physiol. Regul. Integr. Comp. Physiol. 301:R1557-R1568, 2011.
Straub et al., "Stimulation of Insulin Secretion by Denatonium, One of the Most Bitter-Tasting Substances Known " Diabetes 52:356-364, 2003.
Meyerhof et al., "The Molecular Receptive Ranges of Human TAS2R Bitter Taste Receptors" Chem. Senses 35:157-170. 2010.
PCT/US2019/040432 written opinion.

* cited by examiner

ORAL PHARMACEUTICAL FORMULATIONS OF BITTER COMPOUNDS FOR ASTHMA

TECHNICAL FIELD

The present disclosure provides an oral pharmaceutical formulation of bitter compounds that are agonists of TAS2R receptors for the treatment of asthma. More specifically, the present disclosure provides an asthma oral formulation comprising a bitter agent selected from the group consisting of denatonium benzoate (DB), denatonium chloride (DC), denatonium saccharide (DS), denatonium acetate (DA), and combinations thereof, and formoterol.

BACKGROUND

Asthma and chronic obstructive pulmonary disease (COPD) together affect 300 million individuals worldwide. The major source of morbidity and mortality from both diseases is airway obstruction, which in part is due to actively constricted smooth muscle of the bronchi. Although airway resistance in COPD has variable degrees of reversibility, owing to structural changes that result from smoking, therapies for COPD and asthma include antagonists directed at broncho-constrictive receptors and agonists directed at receptors that relax ASM. The major receptor signaling family in ASM that regulates contraction and relaxation are G protein-coupled receptors (GPCRs). There is an ongoing effort to identify GPCR pathways leading to regulation of airway tone, thereby providing new treatment strategies for asthma and COPD. This is particularly relevant because the incidence of both diseases is increasing, and at least one-half of all patients have inadequate control of the disease with currently available agents.

Deshpande et al. (*Nature Medicine* 16:1299-1305, 2010) discovered that the bitter agents tested (quinine and denatonium), when administered by inhalation, were effective in a mouse inhalation model. However, it was extremely difficult to administer a bitter agent by inhalation as the bitter taste, even when inhaled, will be difficult to obtain patient compliance. Therefore, there is a need in the art for orally available bitter agents for asthma that can bypass mouth taste receptors.

Formoterol is a long-acting bronchodilator used as a long-term (maintenance) treatment to prevent or decrease wheezing and trouble breathing caused by asthma or ongoing lung disease (chronic obstructive pulmonary disease—COPD, which includes chronic bronchitis and emphysema). It is used long-term if asthma symptoms are not controlled by other asthma medications (such as inhaled corticosteroids). It works in the airways by relaxing muscles and opening air passages to improve breathing. Formoterol is administered by inhalation.

Formoterol or eformoterol is a long-acting $\beta_2$ agonist (LABA) used in the management of asthma and COPD. It is marketed in three forms: a dry-powder inhaler, a metered-dose inhaler and an inhalation solution, under various trade names including Atock, Atimos/Atimos Modulite, Foradil/Foradile, Oxeze/Oxis, and Perforomist. It is also marketed in the combination formulations budesonide/formoterol and mometasone/formoterol. Formoterol has an extended duration of action (up to 12 h) compared to short-acting $\beta_2$ agonists such as salbutamol (albuterol), which are effective for 4 h to 6 h. LABAs, such as formoterol, are used as "symptom controllers" to supplement prophylactic corticosteroid therapy. A "reliever" short-acting $\beta_2$ agonist (e.g., salbutamol) is still required, since LABAs are not recommended for the treatment of acute asthma.

Accordingly, there is a need in the art for non-inhaled dosages of formoterol and better or more synergistic combinations with formoterol.

SUMMARY

The present disclosure provides an oral pharmaceutical formulation of bitter compounds that are agonists of TAS2R receptors for the treatment of asthma. More specifically, the present disclosure provides surprising data of unpredictability among bitter agents that salts of denatonium (benzoate, saccharide, chloride, acetate and citrate) were far superior to 3-CQL (3-caffeoylquinic acid) another bitter agent tested. Therefore, bitter agent mechanism of action cannot predict efficacy in an in vitro asthma model.

Therefore, the present disclosure provides an asthma treatment oral formulation comprising a bitter agent selected from the group consisting of denatonium benzoate (DB), denatonium chloride (DCl), denatonium saccharide (DS), denatonium acetate (DA), denatonium citrate (DC), denatonium maleate (DM), and combinations thereof. Preferably, the oral formulation further comprises formoterol. Preferably, the bitter agent for an asthma formulation is DB or DA. Preferably the daily dosage of DB or DA for an adult is from about 10 mg to about 400 mg. More preferably, the daily dosage of DB or DA for an adult is from about 10 mg to about 200 mg. Most preferably, the daily dosage of DB or DA for an adult is from about 10 mg to about 100 mg.

The present disclosure further provides a method for treating asthma with an orally administered formulation comprising a bitter agent selected from the group consisting of denatonium benzoate (DB), denatonium acetate (DA), denatonium chloride, denatonium saccharide (DS), and combinations thereof. Preferably, the oral formulation further comprises formoterol.

Preferably, the bitter agent for an asthma formulation is DB or DA. Preferably the daily dosage of DB or DA for an adult is from about 10 mg to about 400 mg. More preferably, the daily dosage of DB or DA for an adult is from about 10 mg to about 200 mg. Most preferably, the daily dosage of DB or DA for an adult is from about 10 mg to about 100 mg.

DETAILED DESCRIPTION

The present invention was discovered by the surprising results (detailed below) that not all bitter agents that are agonists of the same TAS2R receptors are effective when tested using primary human vascular endothelial cells is an in vitro model measuring stimulated smooth muscle contractile ability. Moreover, the data showed synergistic ability to relax stimulated pulmonary vascular smooth muscle cells (PVSMC) when using a TAS2R receptor agonist together with lower concentrations of formoterol. These data show unpredictability of TAS2R receptor agonists as treatments for PAH and synergy of a combination with formoterol, allowing for uses of lower oral doses of formoterol when administered as an oral formulation (preferably capsule) to avoid having a TAS2R agonist come into contacts with bitter taste receptors in the mouth/tongue.

An in vitro model using human airway smooth muscle cells (HASM) from both asthmatic patients and "normal" non-asthmatic humans was stimulated to contract with bradykinin. Surprisingly, it was discovered both that the TAS2R receptor agonist 3-CQL did not relax stimulated PVSMC cells, but another TAS2R receptor agonist denatonium salts (DB and DS) did relax the cells.

The assay investigated bronchodilatation properties of bitter taste agonists, individually and in combination, administered to primary human smooth muscle (HASM) cells after inducing contraction with asthmatic agent bradykinin. HASM cells were obtained from asthmatic patients and "normal" or non-asthmatic patients. Each of 4 primary HASM cell lines (2 from healthy donors; 2 from asthmatic donors) were seeded on FLECSplates and were stimulated to contract via exposure to bradykinin (BK) or carbachol. The general contractile response to this agonist evolved over ~40 minutes before plateauing and reversing. Accordingly, at 15 minutes following exposure to BK, the cells were treated with a denatonium salt or 3-CQL for Example 1, or combinations thereof, as well as positive controls and negative controls. The cells were imaged at 5 minute intervals beginning with a baseline reading, out to 45 minutes. The measurement was attenuation of population wide BK-induced contractility by treatment of a test compound (or combination) relative to controls. Only cells that exhibited robust contractile responses to BK were considered for the analysis. The figures show percent reversal and compared to standard asthmatic treatment formoterol.

Figures 1A, 1B, 1C:
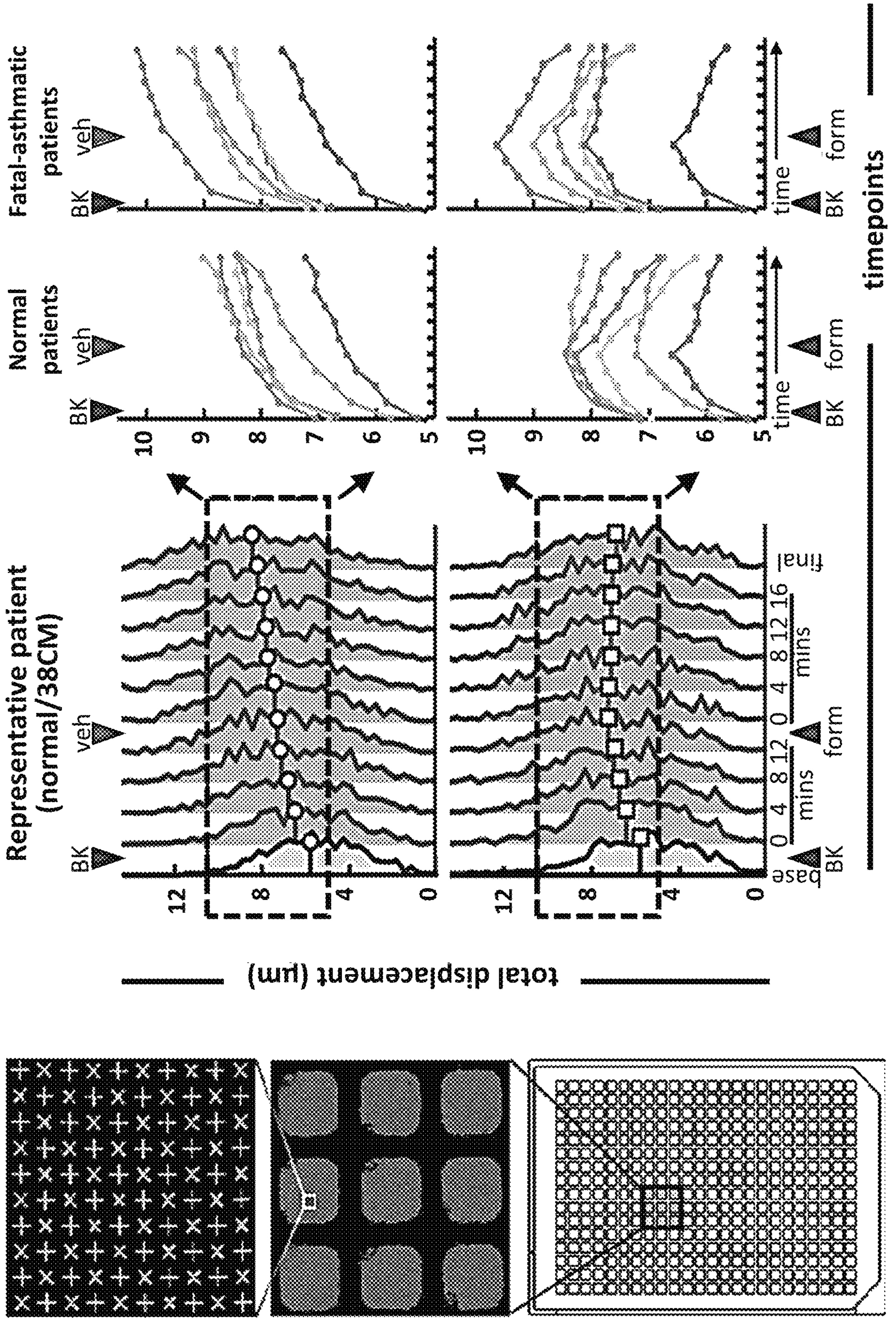
FIGS. 1A, 1B, and 1C show the bronchodilator assay workflow with a 284 well plate of FLECS. Each well holds ~1,200 micro-patterns for sensing force-generation by single cells. In (b) shows a distribution of single-cell contractilities, evolving with time, after exposure to pro-contractile agonist bradykinin (indicated by 'BK' label). In the top panel, DMSO vehicle ('veh'; negative control) is given after time-point 5, producing no effect. In the bottom panel, formoterol ('form'; positive control) is given after time-point 5, causing a halt and reversal in the contraction. The two cases represent the positive and negative controls for the assay. In (c), the experiment explained in (b) is performed for 12 unique patient-derived asthmatic lines, demonstrating robust effects of these agonists (positive controls) and controls.

FIG. 1 shows the assay workflow with a 284 well plate of FLECS. Each well holds ~1,200 micro-patterns for sensing force-generation by single cells. In (b) shows a distribution of single-cell contractilities, evolving with time, after exposure to pro-contractile agonist bradykinin (indicated by 'BK' label). In the top panel, DMSO vehicle ('veh'; negative control) is given after time-point 5, producing no effect. In the bottom panel, formoterol ('form'; positive control) is given after time-point 5, causing a halt and reversal in the contraction. The two cases represent the positive and negative controls for the assay. In (c), the experiment explained in (b) is performed for 12 unique patient-derived asthmatic lines, demonstrating robust effects of these agonists (positive controls) and controls.

Figure 2:
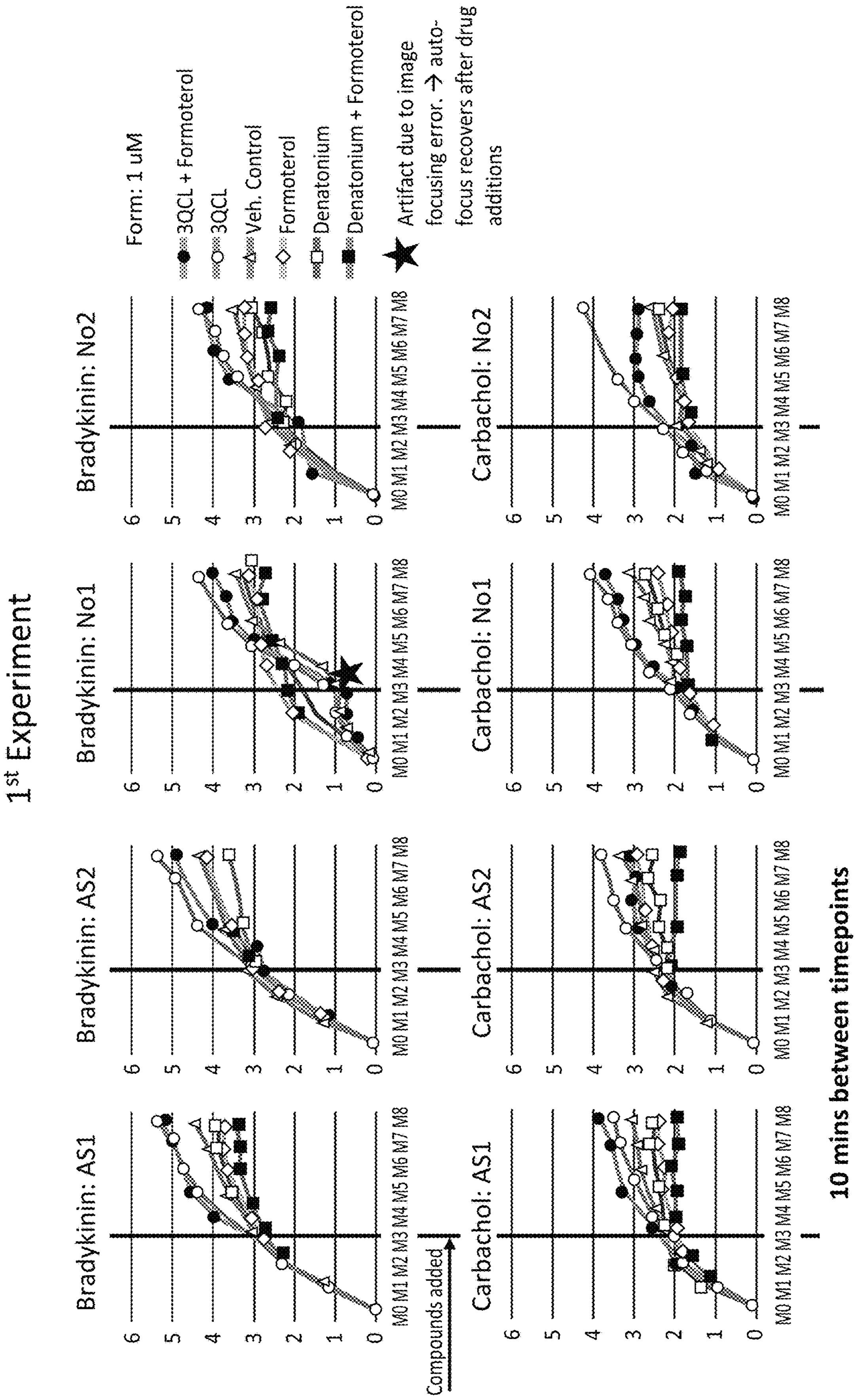
In FIG. 2, both 3-CQL (100 μM) and DB (100 μM) were tested alone and in combination with formoterol (1 μM). The negative control was 0.1% DMSO in medium. The stimulating agents were BK and carbachol (10 μM). The data was collected from combined cells from four wells per condition, and each trace was from about 1200 to 1500 cells (standard error of mean was small). The data show that 3-CQL was, surprisingly, shown to increase contraction relative to control (meaning it exacerbates asthma, rather than treats it). But DB had a relaxing effect. There was a synergistic effect of DB and formoterol. Formoterol alone was not as potent as previous experiments since its concentration was reduced 50×.

In FIG. 2, both 3-CQL (100 μM) and DB (100 μM) were tested alone and in combination with formoterol (1 μM). The negative control was 0.1% DMSO in medium. The stimulating agents were BK and carbachol (10 μM). The data show that 3-CQL was, surprisingly, shown to increase contraction relative to control (meaning it exacerbates asthma, rather than treats it). But DB had a relaxing effect.

Figure 3:
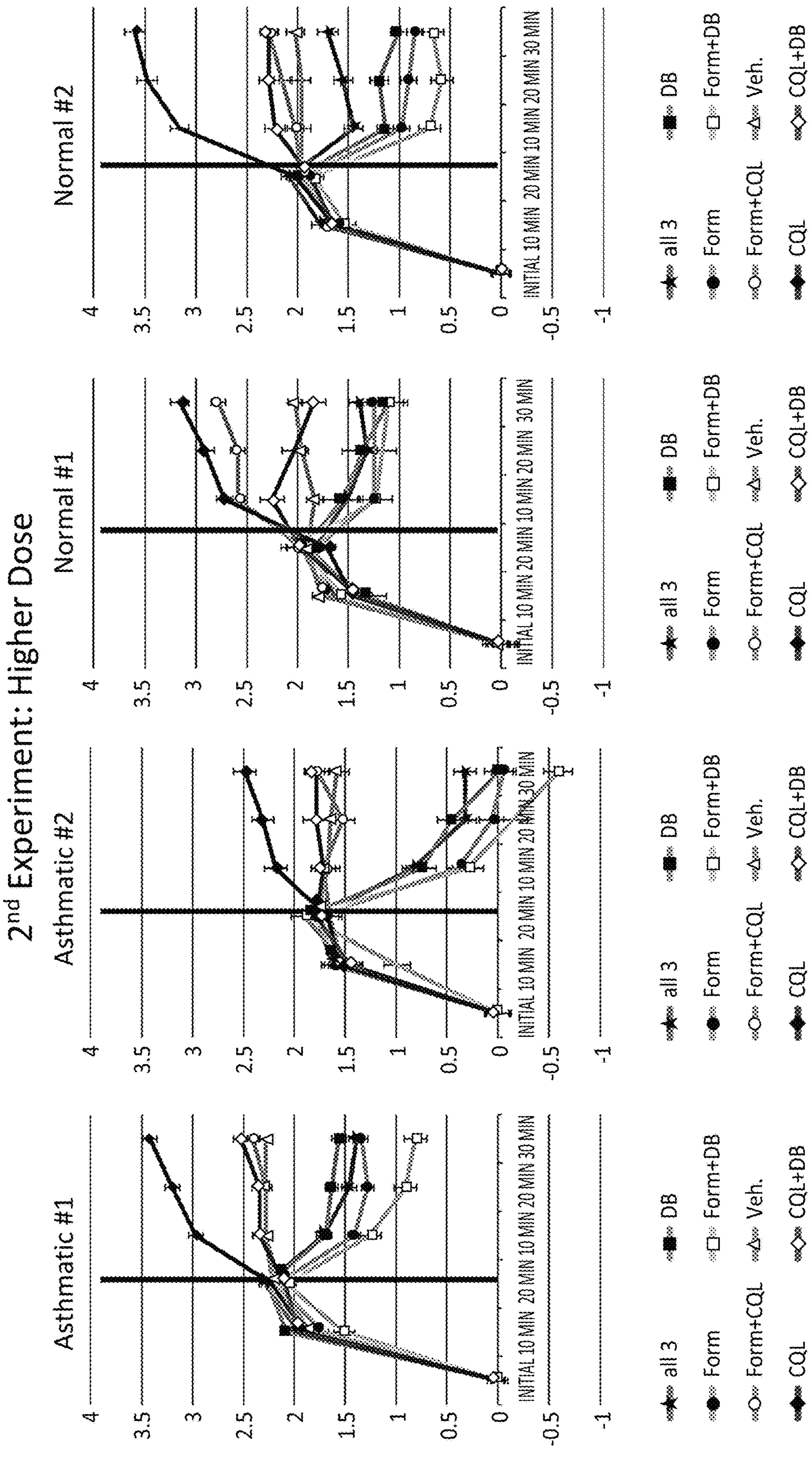
In FIG. 3, higher doses were tested. 3-CQL (1.0 mM); Denatonium benzoate (1.0 mM); 3-CQL+Formoterol (1.0 mM, 50 μM); Denatonium+Formoterol (1.0 mM, 50 μM); 3-CQL+Denatonium+Formoterol (1.0 mM, 1.0 mM, 50 μM); 3-CQL+Denatonium (1.0 mM, 1.0 mM). Positive control was 50 μM Formoterol and the negative control was 0.5% DMSO in medium. The data show synergy for the combination of DB plus formoterol at these higher concentrations for cells coming from asthmatic patients. Each trace was data from four wells combined. The error bars represent standard error of mean.
Figure 4:
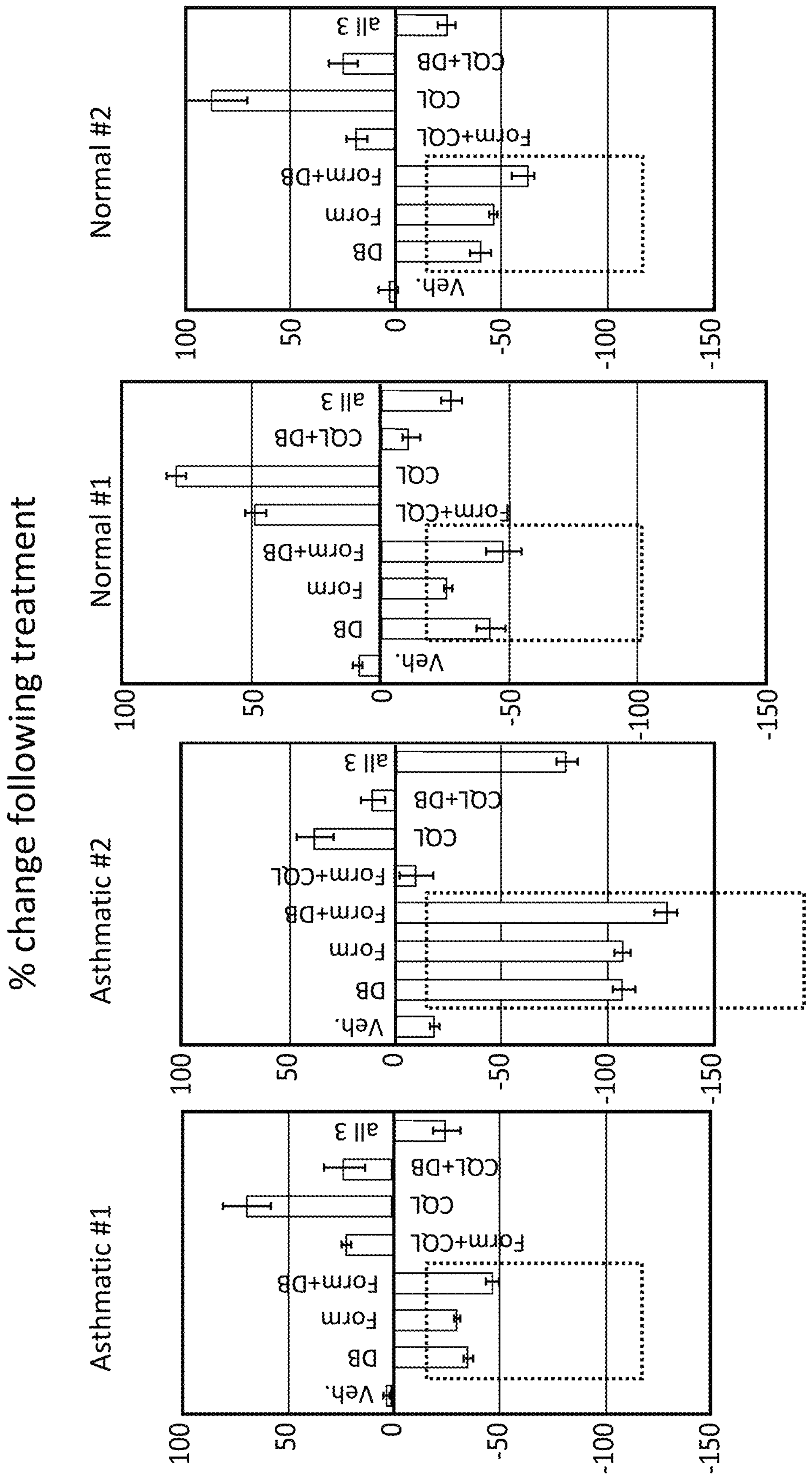
In FIG. 4, the data are presented in bar graph format.

In FIG. 3, higher doses were tested. 3-CQL (1.0 mM); Denatonium benzoate (1.0 mM); 3-CQL+Formoterol (1.0 mM, 50 μM); Denatonium+Formoterol (1.0 mM, 50 μM); 3-CQL+Denatonium+Formoterol (1.0 mM, 1.0 mM, 50 μM); 3-CQL+Denatonium (1.0 mM, 1.0 mM). Positive control was 50 μM Formoterol and the negative control was 0.5% DMSO in medium. The data show synergy for the combination of DB plus formoterol at these higher concentrations for cells coming from asthmatic patients. In FIG. 4, the data are presented in bar graph format.

TABLE 1

| Bitter agents | |
|---|---|
| Denatonium salts | Chemical structure |
| Denatonium Benzoate (DB) | 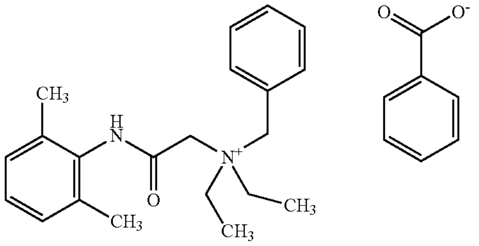 |

TABLE 1-continued

| Bitter agents | |
|---|---|
| Denatonium salts | Chemical structure |
| Denatonium Saccharide (DS) | 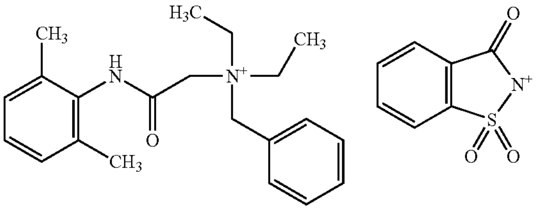 |

Denatonium benzoate ("DB"). Molecular formula: $C_{28}H_{34}N_2O_3$ Mass: 446.581 Da IUPAC name: phenylmethyl-[2-[(2,6-dimethylphenyl)amino]-2-oxoethyl]-diethylammonium benzoate ChemSpider ID: 18392

Denatonium, usually available as denatonium benzoate (under trade names such as BITTERANT-b, BITTER+PLUS, Bitrex or Aversion) and as denatonium saccharide (BITTERANT-s), is believed to be the most bitter chemical compound known, with bitterness thresholds of 0.05 ppm for the benzoate and 0.01 ppm for the saccharide. It is used as an aversive agent (bitterants) to prevent inappropriate ingestion. Denatonium is used in denatured alcohol, antifreeze, nail biting preventions, respirator mask fit-testing, animal repellents, liquid soaps, and shampoos. It is not known to pose any long-term health risks.

An ideal bitter compound therapeutic should be safe to consume in the quantities required to elicit the desired physiologic response, and also activate a broad range of TAS2R receptor subtypes. Denatonium benzoate (DB) is a bitter substance, and it activates 8 TAS2R subtypes. It is also generally regarded as safe and is commercially added to toxic household products to discourage inadvertent consumption by children.

We claim:

1. A synergistic formulation comprising a bitter agent and formoterol, wherein the bitter agent is chosen from denatonium acetate (DA), denatonium citrate (DC), denatonium maleate (DM), and combinations thereof, wherein the formulation is formulated for oral administration and is suitable for treating asthma.

2. The formulation of claim 1, wherein the bitter agent for an asthma formulation is DA.

3. A dose of the formulation of claim 2, comprising a dosage of DA of from about 10 mg to about 400 mg.

4. The dose of claim 3, wherein the dosage is from about 10 mg to about 200 mg.

5. The dose of claim 4, wherein the dosage of DA is from about 10 mg to about 100 mg.

6. A method for treating asthma, comprising orally administering a synergistic formulation comprising a bitter agent and formoterol to a subject having asthma, wherein the bitter agent is chosen from denatonium acetate (DA), denatonium citrate (DC), denatonium maleate (DM).

7. The method of claim 6, wherein the bitter agent is DA.

8. The method of claim 7, wherein the subject is an adult and the daily dosage of DA is from about 10 mg to about 400 mg.

9. The method of claim 8, wherein the subject is an adult and the daily dosage of DA is from about 10 mg to about 200 mg.

10. The method of claim 9, wherein the subject is an adult and the daily dosage of DA is from about 10 mg to about 100 mg.

11. The method of claim 6, wherein the subject is a human.

12. The method of claim 6, wherein the subject is an adult human.

* * * * *